United States Patent
Caillat et al.

(10) Patent No.: US 11,325,126 B2
(45) Date of Patent: May 10, 2022

(54) DEVICE FOR PREPARING A BLOOD SAMPLE

(71) Applicant: COMMISSARIAT A L'ENERGIE ATOMIQUE ET AUX ENERGIES ALTERNATIVES, Paris (FR)

(72) Inventors: Patrice Caillat, Seyssins (FR); Anne-Gaelle Bourdat, Nantoin (FR); Virginie Brun, Noyarey (FR); Benoit Gilquin, Saint-Egreve (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 580 days.

(21) Appl. No.: 16/086,193

(22) PCT Filed: Mar. 14, 2017

(86) PCT No.: PCT/FR2017/050583
§ 371 (c)(1),
(2) Date: Sep. 18, 2018

(87) PCT Pub. No.: WO2017/162956
PCT Pub. Date: Sep. 28, 2017

(65) Prior Publication Data
US 2020/0197939 A1    Jun. 25, 2020

(30) Foreign Application Priority Data
Mar. 21, 2016 (FR) .................... 1652415

(51) Int. Cl.
*B01L 3/00* (2006.01)
*G01N 1/34* (2006.01)

(52) U.S. Cl.
CPC ........ *B01L 3/502761* (2013.01); *G01N 1/34* (2013.01); *B01L 2200/0631* (2013.01);
(Continued)

(58) Field of Classification Search
CPC ....... B01L 2300/087; B01L 2300/0867; B01L 2300/0864; B01L 3/502753;
(Continued)

(56) References Cited

U.S. PATENT DOCUMENTS 7,217,367 B2 * 5/2007 Huang .............. G01N 30/6095
137/625.46
8,227,747 B2 * 7/2012 Roukes .................. B82Y 15/00
250/282
(Continued)

FOREIGN PATENT DOCUMENTS

WO    WO 2007/112114 A2    10/2007

OTHER PUBLICATIONS

List of references cited in ISR issued Jun. 30, 2017, in PCT/FR2017/050583, filed Mar. 14, 2017, (1 page).

*Primary Examiner* — Shogo Sasaki
(74) *Attorney, Agent, or Firm* — Oblon, McClelland, Maier & Neustadt, L.L.P.

(57) ABSTRACT

A device for preparing a blood sample, including a microfluidic card including: a first chamber for separating and/or extracting proteins to be analyzed that are present in the blood sample; a second chamber used for an operation involving digestion of proteins of different species that are present in the sample, to obtain a second sample containing digested peptides and nondigested proteins; and a third chamber connected to the second chamber to receive the second sample containing the digested peptides and the non-digested proteins, the third chamber being used for an operation involving purification and stabilization of the digested peptides.

19 Claims, 3 Drawing Sheets

(52) U.S. Cl.
CPC ... *B01L 2200/0652* (2013.01); *B01L 2200/16* (2013.01); *B01L 2300/087* (2013.01); *B01L 2300/0816* (2013.01); *B01L 2300/0864* (2013.01)

(58) Field of Classification Search
CPC ....... B01L 2300/0816; B01L 3/502761; B01L 2200/16; B01L 2200/0631; B01L 2200/0652; G01N 33/48; G01N 1/34
See application file for complete search history.

(56) References Cited

U.S. PATENT DOCUMENTS

| | | |
|---|---|---|
| 2004/0175822 A1 | 9/2004 | Timperman |
| 2007/0017812 A1* | 1/2007 | Bousse ............ G01N 27/44743 204/601 |
| 2007/0292941 A1 | 12/2007 | Handique et al. |
| 2009/0130719 A1* | 5/2009 | Handique ............. B01L 3/5025 435/91.2 |
| 2009/0261241 A1* | 10/2009 | Roukes ............... H01J 49/0018 250/282 |
| 2015/0328638 A1 | 11/2015 | Handique et al. |

\* cited by examiner

DEVICE FOR PREPARING A BLOOD SAMPLE

TECHNICAL FIELD OF THE INVENTION

The present invention relates to a device for preparing a blood sample and to a system employing said device for the preparation of a blood sample. The invention also relates to a process for preparing a blood sample used with said device.

PRIOR ART

Proteomic analysis based on mass spectrometry to detect and assay proteins in biological samples such as plasma is increasingly widespread since it is particularly efficient. However, in order for this analysis to be optimal and reliable, the analyzed blood sample needs to be perfectly stable. Now, it turns out, for example, that the time which elapses between the collection of a blood sample, its preparation (for the production of the serum or plasma fraction) and its transfer to an analytical laboratory is very variable, thus giving analytical results of diverse qualities. Specifically, the natural process of degradation of the proteins of interest present in plasma may be more or less advanced depending on the time which has elapsed between the collection of the sample and its transfer to the analytical laboratory, which leads to a certain amount of variability in the results obtained.

Patent application US 2004/175822 A1 describes a method for automating Edman degradation via the use of a microfluidic card. It requires the deposition into the sequencer of a pure (or very highly enriched) protein or a peptide to enable the determination of the protein's amino acid sequence by chemical digestion of one of the ends. Prior to this phase, it is thus necessary to separate the proteins (for example on a gel) and to introduce them one by one into the machine.

The aim of the invention is to propose a device which is employed for preparing and stabilizing a blood sample, this device allowing a blood sample to be processed efficiently by reducing the time which elapses between the collection of the blood and the stabilization of the sample, so as to obtain good-quality and perfectly reproducible results. The solution of the invention also makes it possible to conserve throughout the preparation process the complexity of the plasmatic proteome (several hundred different protein species).

DESCRIPTION OF THE INVENTION

This aim is achieved by a device for preparing a blood sample, comprising a microfluidic card which includes:
- an injection channel via which said blood sample may be injected,
- a first chamber into which said injection channel emerges, said first chamber being intended for performing an operation of separation and/or extraction of proteins to be analyzed present in said blood sample,
- a second chamber connected to said first chamber so as to receive a first sample comprising proteins of different species, said second chamber being intended for performing an operation of digestion of the proteins to be analyzed which are present in order to obtain a second sample including digested peptides and undigested proteins,
- a third chamber connected to said second chamber so as to receive said second sample including the digested peptides and the undigested proteins, said third chamber being intended for performing an operation of purification and stabilization of the digested peptides.

In contrast with prior art mentioned above, the aim of the invention is different since there is no individual separation. The device of the invention makes it possible to prepare a blood sample while conserving the complexity of the plasmatic proteome (several hundred different protein species), and to prepare them for their subsequent analysis while remaining global and in a single passage. This conserved complexity of the protein sample is incompatible with the Edman method since, on each cycle of the sequencing, several amino acids would be identified simultaneously, which would prevent any identification.

According to a particular feature, the device includes a depletion support present in the first chamber for taking up the majority proteins present in said blood sample.

According to one configuration, the depletion support includes beads present in the first chamber and grafted with one or more uptake components suited to the majority proteins to be taken up.

According to another configuration, the depletion support includes pillars positioned in the first chamber and grafted with one or more uptake components suited to the majority proteins to be taken up.

According to another particular feature, the first chamber is made, for example, in the form of a coil whose functionalized surfaces form the depletion support.

According to one implementation variant, the device includes an enrichment support present in the first chamber for binding and enriching the proteins to be analyzed present in the blood sample. The enrichment support includes, for example, beads present in the first chamber and grafted with one or more enrichment components suited to the proteins to be enriched.

According to one implementation variant, the enrichment support includes pillars positioned in the first chamber and grafted with one or more enrichment components suited to the proteins to be enriched.

According to another possible implementation variant, the first chamber is made in the form of a coil whose surfaces form the enrichment support.

According to a particular feature, the second chamber includes a surface at least partially covered with an enzyme or a mixture of enzymes for performing the digestion operation.

As an implementation variant, the second chamber includes an internal volume intended to store an enzyme or a mixture of enzymes in lyophilized form for performing the digestion operation.

According to one implementation variant, the device may include an intermediate stabilization chamber located downstream of said first chamber and upstream of the second chamber and intended for stabilizing the proteins extracted in the first chamber.

According to another implementation variant, the device may also include an initial separation chamber, located upstream of the first chamber when the first chamber is intended for protein extraction.

According to another implementation variant, the device may, depending on its configuration, include specific separation means arranged to separate the plasma and the blood cells present in the blood sample, arranged upstream of the first chamber.

According to a particular feature, the device includes a reverse-phase liquid chromatography column housed in the third chamber to attach, stabilize and/or separate the digested peptides.

Advantageously, the device includes several secondary channels made in the card and distributed to emerge in each chamber.

The invention also relates to a system for preparing a blood sample, comprising a programmable robot, which includes a device for preparing a blood sample as defined above. The programmable robot includes a processing unit intended to run software modules suitable for generating commands intended for actuators in a given sequence as a function of the various steps of preparation of the blood sample on said device.

The invention also relates to a process for preparing a blood sample, performed in the preparation device as defined above. This process includes the following steps:
- extraction in the first chamber of proteins to be analyzed which are present in said blood sample and/or separation to separate the plasma from the blood cells in the blood sample,
- digestion in the second chamber of the proteins to be analyzed which are present in a first sample comprising proteins of different species to be analyzed for the purpose of obtaining a second sample including digested peptides and undigested proteins,
- separation in the third chamber between the digested peptides and the undigested proteins.

According to a particular feature, the extraction step is performed by depletion of the majority proteins of the plasma or enrichment in the proteins to be analyzed.

According to another particular feature, the stabilization step is advantageously performed by liquid chromatography on a column of reverse-phase type.

BRIEF DESCRIPTION OF THE FIGURES

Other characteristics and advantages will appear in the detailed description which follows with regard to the attached drawings, in which.

DETAILED DESCRIPTION OF AT LEAST ONE EMBODIMENT

The invention relates in particular to a device for preparing a blood sample, before its analysis, for example by liquid chromatography associated with quantitative mass spectrometry. The device of the invention will make it possible in particular to prepare and store a stabilized sample intended for subsequent analysis, without any risk of degradation of the sample.

The term "stabilized sample" especially means a sample that is not sensitive to a protease action.

In the rest of the description, in a nonlimiting manner, the device of the invention will be described for a preparation using a plasmatic sample derived from the blood sample collected from the patient, but it should be understood that it could be employed for a preparation using the serum derived from the sample.

In the rest of the description, the term "chamber" means a space defining a nonzero closed or partially closed volume into which one or more channels may emerge.

The device mainly includes a microfluidic card C which includes channels and several chambers each contributing to the preparation of the blood sample before analysis. This device may be employed in a more global blood preparation system. This system in particular includes a programmable robot, referenced A, which controls the preparation of the blood sample on the card C.

As described above, the device of the invention includes a microfluidic card C having, for example, the format of a credit card, in which all the steps leading to the preparation and stabilization of the sample before its analysis may be performed.

The microfluidic card C is, for example, placed in a suitable housing of the programmable robot A. The programmable robot A advantageously includes a processing unit arranged to control all the steps required for the preparation of the blood sample on said card. The processing unit runs software modules each intended to control one or more of these steps. These software modules are run to generate output commands intended for various actuators. These actuators may be, for example, micropumps, magnetic stirring systems, heating systems, cooling systems, ultrasound or microwave emission systems, or microfluidic valves. These various actuators form, for example, part of the system of the invention employed for the preparation of the blood sample in the card.

This microfluidic card C is made, for example, using two plates bonded together and on each of which are formed the units forming the chambers and the fluidic pathways of the card. The card C is made, for example, of a transparent material such as PMMA, polycarbonate or COC ("cyclic olefin copolymer"). The microfluidic card C will be described below in connection with the various steps for preparing a blood sample defined below.

Figure 1:
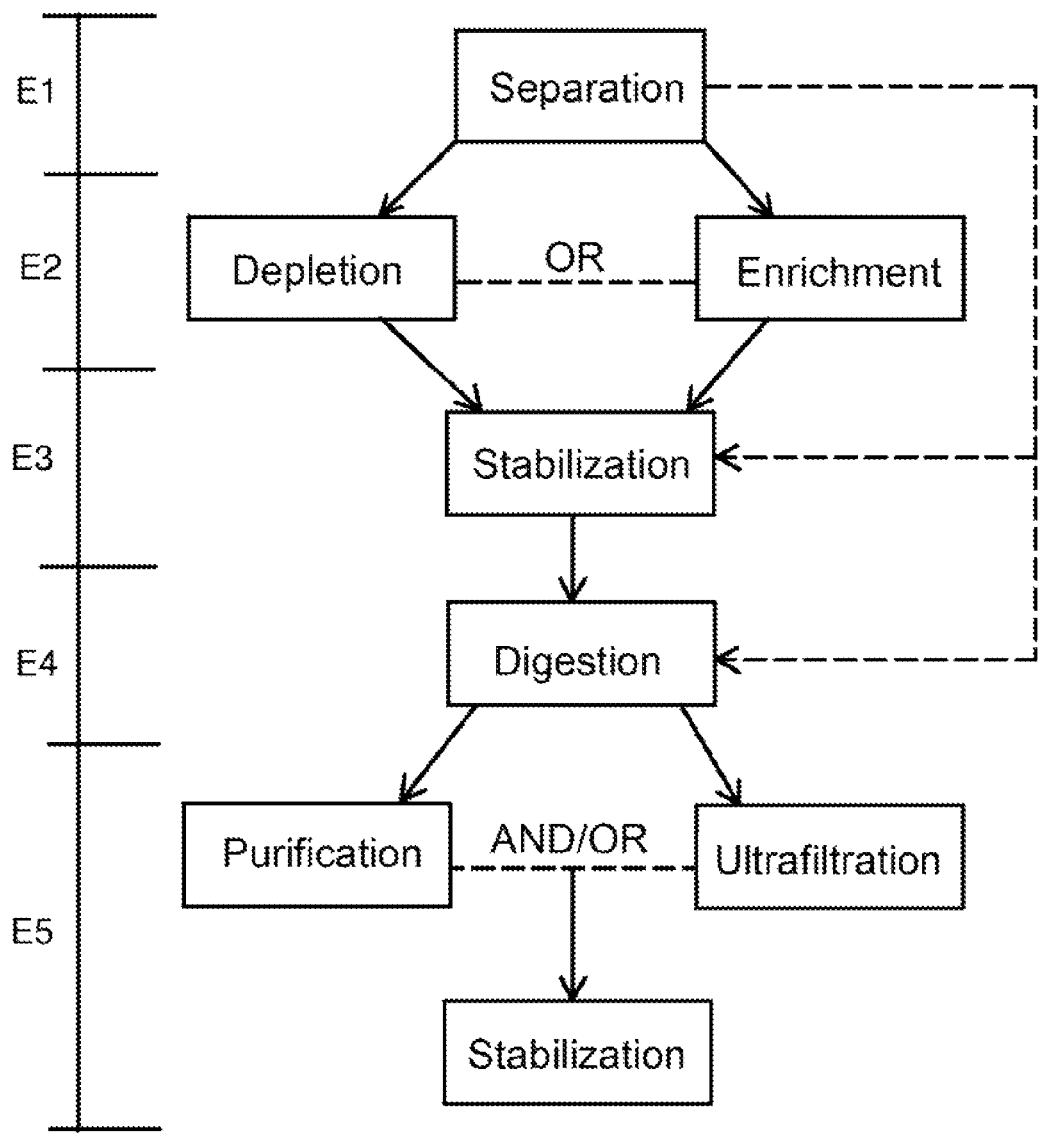
FIG. 1 represents a diagram showing the various steps of a process for preparing a blood sample.

With reference to FIG. 1, the microfluidic card is arranged to perform the steps for preparing the sample. Depending on the steps that are performed, the microfluidic card C may take various microfluidic structures.

With reference to the attached figures, the microfluidic card C mainly includes:
- an injection channel IN via which said blood sample may be injected;
- several successive chambers connected together via channels;
- secondary injection or extraction channels S1, S2 connected to the various chambers, for example for injecting washing solutions or for extracting waste from the chambers.

Valves suitably positioned on the card C are controlled by the programmable robot A to control the various steps for preparing the blood sample on the card.

Moreover, micropumps (not shown) are also controlled by the programmable robot 2 to make the sample pass from one chamber to another, by suction or injection.

The programmable robot 2 thus includes several output modules each intended for controlling a separate actuator, such as each valve V or each micropump.

More precisely, the injection channel IN is intended to receive the blood sample collected from the patient. The tube containing the blood sample will be connected, for example, to the inlet of the injection channel IN. This inlet may be made according to different implementation variants depending on the chosen type of fluidic connection. Various types of connection may in fact be envisaged, for example employing a module of "Saf-T Wing" (registered trademark) type. The injection of the blood sample into the injection channel IN will be controlled, for example, by a first valve controlled by the robot and activated by a micropump controlled by the robot. The initial blood sample collected from the patient's arm will be, for example, from 2 to 10 milliliters. The analysis will be performed on a few microliters to 50 µl of plasma (or of serum) contained in this sample.

With reference to FIGS. 2A to 2E, according to the steps performed, the microfluidic card may include three chambers, four chambers or five chambers.

Figure 2A:
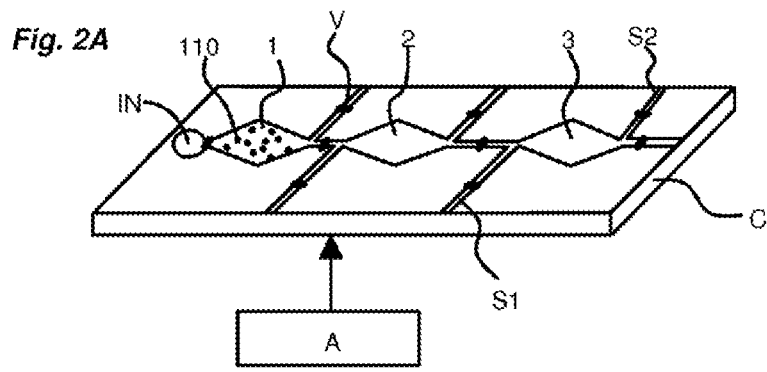
FIGS. 2A to 2E represent several implementation variants of a system for preparing a blood sample, including a device for preparing the blood sample according to the invention.

In a configuration with three chambers, shown in FIG. 2A, the microfluidic card C includes:
 a first depletion/enrichment chamber 1,
 a second digestion chamber 2, and
 a third stabilization chamber 3.

Figure 2B:
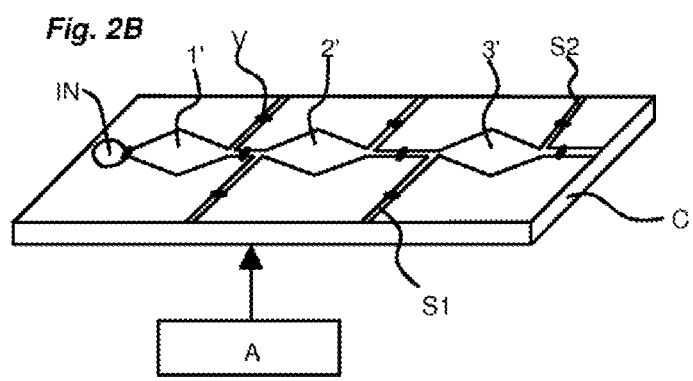

In another configuration with three chambers, shown in FIG. 2B, the microfluidic card C includes:
 a first separation chamber 1',
 a second digestion chamber 2', and
 a third stabilization chamber 3'.

Figure 2C:
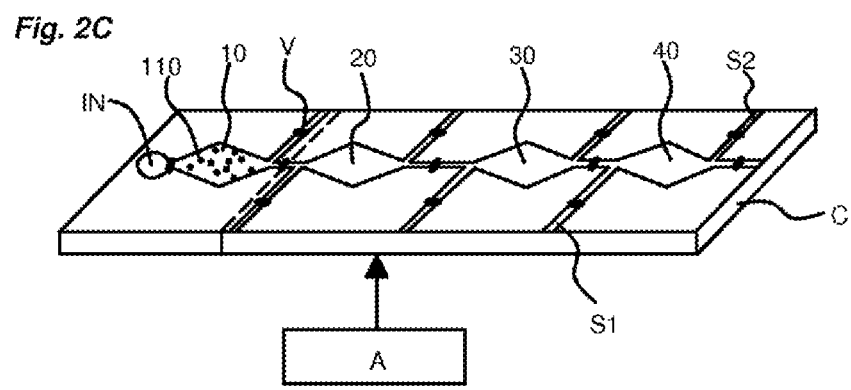

In a configuration with four chambers, shown in FIG. 2C, the microfluidic card C includes:
 a first separation and/or depletion/enrichment chamber 10,
 a second stabilization chamber 20,
 a third digestion chamber 30, and
 a fourth stabilization chamber 40.

Figure 2D:
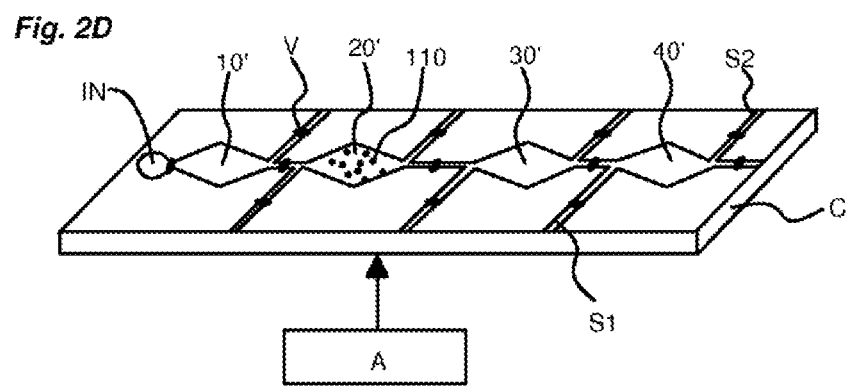

In another configuration with four chambers, shown in FIG. 2D, the microfluidic card includes:
 a first separation chamber 10',
 a second depletion/enrichment chamber 20',
 a third digestion chamber 30', and
 a fourth stabilization chamber 40'.

Figure 2E:
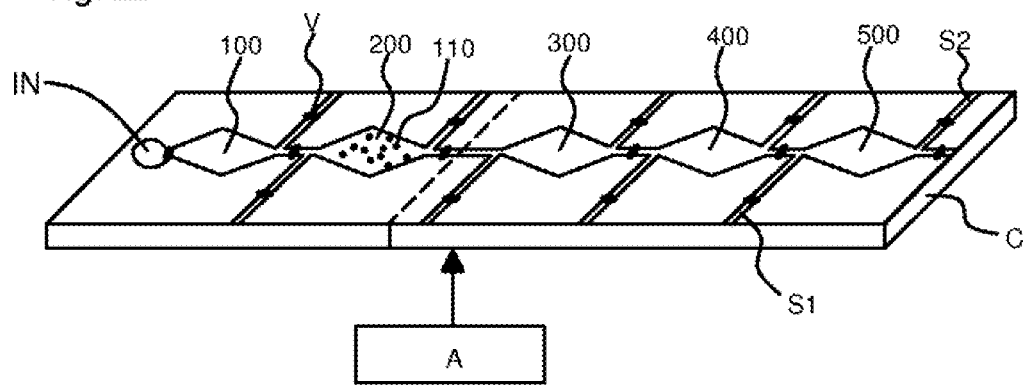

In a configuration with five chambers, shown in FIG. 2E, the microfluidic card includes:
 a first separation chamber 100,
 a second depletion/enrichment chamber 200,
 a third stabilization chamber 300,
 a fourth digestion chamber 400, and
 a fifth stabilization chamber 500.

For each chamber, the device of the invention advantageously includes a valve V located upstream and a valve located downstream so as to control the passage of the sample from one chamber to another. Each valve V is advantageously controlled by the programmable robot A.

The device advantageously includes a secondary injection channel S1 emerging into each chamber, employed especially to inject compounds into the chamber or washing or elution solutions, and a secondary extraction channel S2 employed, for example, to extract waste from the chamber. Injection into a chamber and extraction from a chamber are performed by valves V and micropumps controlled by the programmable robot A.

The preparation of the sample may be performed for the purpose of qualification of the proteins present in the sample and/or quantification. For the purpose of quantification the volume of sample injected into the device must be calibrated so as to work on a known volume. Various calibration means may be envisaged. It will be a matter, for example, of controlling the upstream and downstream valves of the first chamber to adjust the volume and/or by setting the volume of the first chamber. The downstream valve of the first chamber is closed and the sample is then injected into the chamber until it is full.

With reference to FIG. 1 and FIGS. 2A to 2D, the microfluidic device of the invention and its use for performing a process for preparing a blood sample are explained below.

The preparation of the blood sample advantageously starts with a first separation step E1.

In this first step E1 defined in FIG. 1, to perform separation between the plasma and the blood cells in the blood sample, several solutions may be envisaged, taken alone or in combination with each other:
 a first solution consists in performing the separation in a first chamber 1', 10, 10', 100 dedicated to this step, using a polymer, for example a polymer of Dacron (registered trademark) type which allows separation by filtration between the plasma and the cells;
 a second solution consists in employing a filtering membrane of Vivid (registered trademark) type placed on the path of the injection channel IN or directly on the cartridge which initially includes the blood sample to be analyzed and which is positioned on the inlet of the channel during the injection of the blood sample. This will be the case with a microfluidic card made according to the variant of FIG. 2A or 2C. The sampling cartridge advantageously forms part of the preparation system of the invention;
 a third solution consists in employing a capillary microchannel into which the blood sample is injected. This will be the case with a microfluidic card made according to the variant of FIG. 2A or 2C. This microchannel will advantageously be positioned on the injection channel 100;
 a fourth solution consists in performing the separation in a chamber also devoted to the depletion or enrichment step described below. This will be the case, for example, with a microfluidic card made according to the variant of FIG. 2C.

The second step E2 defined in FIG. 1 consists in performing a depletion of the major proteins present in the plasma sample to take them up or enrichment in the proteins to be analyzed which are present in this sample. It will then be a matter of simplifying the blood sample as best as possible and of setting aside certain major proteins, such as albumin, immunoglobulin of A, M or G type, complement proteins, cicatrization proteins, etc. This list is not limiting and simplification of the sample will make it possible, if necessary, to gain in depth of analysis. Needless to say, it will, however, be a matter of conserving a plurality of proteins of different species.

This step is preferentially performed in a depletion or enrichment chamber 1, 10, 20', 200 of the microfluidic card C. The operation for depletion of the major proteins present in the plasma is performed, for example, by employing a support for taking up one or more major proteins present in the plasma sample, for instance albumin. As shown in the figures, this support will be, for example, magnetic beads 110 housed and maintained in their chamber or injected via a suitable channel (of S1 type) into the chamber by means of a command sent by the programmable robot 2. The magnetic beads 110 employed will be grafted with components for taking up the major proteins so as to trap them in the first chamber. They will be, for example:
 magnetic beads grafted with Cibacron Blue for taking up albumin, and/or magnetic beads grafted with protein A for taking up G class immunoglobulins, and/or beads grafted with antibodies or ligands for specifically taking up major proteins of plasma.

As an implementation variant or in addition to the beads 110 employed in the chamber, the uptake support may include pillars positioned in the chamber, the surface of which is coated with one or more of the uptake components mentioned above. The pillars are fixed in the chamber and astutely positioned so that the plasma sample flows between the pillars and comes into contact therewith to take up a maximum amount of the major proteins.

In addition to or in replacement for the beads 110 and/or the pillars mentioned above, the surfaces of the chamber may be coated with one of the uptake components mentioned above so as to trap the major proteins. The form and configuration of the chamber are then optimized to maximize the surfaces for exchange between the plasma sample and the walls which define the internal volume of the chamber. Advantageously, to maximize the surfaces for exchange, the chamber is made in the form of a coiled channel.

It is thus understood that the various means and arrangements envisaged on the microfluidic card C and described above for trapping the major proteins may be astutely combined with each other for the purpose of obtaining a better result. It will be a matter, for example, of using a coiled channel whose surfaces are coated with one or more components for taking up the major proteins, this channel emerging into the chamber in which are placed beads and/or pillars as described above.

In the case where an operation for enrichment in the targeted minor proteins is performed in replacement for an operation for depletion of the major proteins present in the plasma sample, the enrichment support is grafted with specific antibodies. As for depletion, the support may be constituted and arranged according to one of the variants described above for the depletion operation. After washes, the fraction bound to the enrichment support employed will be eluted into the following chamber.

Once the depletion or enrichment operation has been performed, an optional third step E3 consists in stabilizing the target proteins. The aim of this stabilization step E3 is especially to divide the preparation of the blood sample into two phases. If the preparation of the blood sample cannot be finalized within a short space of time, this stabilization step may prove to be necessary. The stabilization is advantageously performed in a dedicated chamber. This stabilization operation may be performed according to different implementation variants:

by precipitation. An alcohol or an acid is injected into the chamber and the precipitate is then filtered so as to retain only the stabilized proteins in the chamber;

by drying, for example by heating and/or injecting air into the chamber.

This stabilization step is performed in a stabilization chamber 20, 300 present in a microfluidic card as shown in FIGS. 2C and 2E.

To restart the preparation process after this stabilization step, a new solubilization of the proteins present in the chamber will be necessary. It will then be a matter of ordering the injection of a solution via a secondary channel of S1 type emerging into the stabilization chamber 20, 300.

A fourth step E4 for preparing the blood sample then consists of an operation for digestion of the target proteins.

This step is performed in a chamber 2, 2', 30, 30', 400 which is devoted to the digestion of the target proteins contained in the plasmatic sample present. To perform this digestion, the programmable robot 2 orders the injection of an enzyme, for instance trypsin, or a mixture of proteolytic enzymes, via a specific secondary channel of S1 type which emerges into said chamber. The programmable robot then orders a magnetic stirring system and a heating system to heat the chamber to a given temperature so as to ensure the protein digestion reaction. As an implementation variant or in addition, the surface of the second chamber may be coated with the enzyme or the mixture of enzymes required for the digestion. In another implementation variant or in addition, it may be imagined that the enzyme or the mixture of enzymes is present in the space formed by the second chamber, for example in a lyophilized form.

Once the digestion operation has been completed in the devoted chamber, the plasma sample which then contains digested peptides and undigested proteins is transferred into a final stabilization chamber 3, 3', 40, 40', 500. This is then the fifth step E5 of the process for preparing the blood sample.

This chamber is devoted to the attachment of the digested peptides for the purpose of separating them and purifying them. To do this, use is made, for example, of a reverse-phase liquid chromatography column, for example of C4 or C18 type, on which the digested peptides are retained and may be washed and then stabilized. A washing liquid may be injected into the chamber via a secondary channel S1 emerging into the chamber and controlled by a valve. In addition or as an implementation variant, it is possible to perform an ultrafiltration operation which makes it possible to retain the undigested proteins and to select only the digested peptides for the purpose of stabilizing them. This filter will be positioned, for example, at the outlet of the preceding chamber. It may prove to be necessary to establish a pressure to push the sample through this filter. The filter will thus be adapted so as to allow the passage only of the digested peptides and to retain the other compounds.

During this fifth step E5, the digested peptides are stabilized in the microfluidic card. The stabilization may be performed via various methods, for example by binding to resin of C4 or C18 type, by drying, by freezing, etc. To stabilize them, the programmable robot A sends an order to a cooling system or to a system for drying by heating or by passing air through, arranged to act on the last chamber for the purpose of stabilizing the peptides present.

Once the peptides have been stabilized, they may be conserved in the card, in the last chamber or in a specific storage chamber (not shown).

For their analysis, for example by mass spectrometry, the peptides that have been stabilized (by drying, freezing or any other suitable method, etc.) are either eluted from the card 1 or directly loaded onto a resin or a reverse-phase liquid chromatography column of C4 or C18 type present in the stabilization chamber.

In other words, the various configurations below will thus be present:

a microfluidic card C as shown in FIG. 2A is arranged to perform steps E2, E4 and E5 described above, a microfluidic card C of FIG. 2B is arranged to perform steps E1, E4 and E5, a microfluidic card C of FIG. 2C is arranged to perform steps E1, E3, E4 and E5, a microfluidic card C of FIG. 2D is arranged to perform steps E1, E2, E4 and E5, a microfluidic card C of FIG. 2E is arranged to perform steps E1, E2, E3, E4 and E5.

Advantageously, the microfluidic card may be splittable (dashed lines P in FIGS. 2C and 2E), especially when it includes an intermediate stabilization chamber. After the proteins have been stabilized in this chamber, the microfluidic card C is sectioned into a first part located upstream of this stabilization chamber and a second part located downstream of this chamber. The analysis may thus be subsequently resumed with the second part of the card comprising the stabilized proteins in its stabilization chamber.

Advantageously, a protein standard (with a labeled isotope), placed before the second step E2, or a peptide standard, placed after the digestion step E4 and before the stabilization step E5, may be injected into the card via a secondary channel S1. This standard of known quality and quantity will make it possible in particular to better establish comparisons with the compounds present in the collected blood sample. This principle is described in particular in the published patent application referenced WO 2008/145763 A1.

Advantageously, the microfluidic device of the invention includes means for recovering the stabilized peptides in the last chamber of the card C. The device thus includes, for example, a perforable membrane of septum type, closing off an aperture emerging into the last chamber of the card. Once the stabilized peptides are in the last stabilization chamber, said membrane is perforated to access the interior of the chamber. The peptides are, for example, extracted from the chamber by suction or any other suitable means.

Figure 3A:
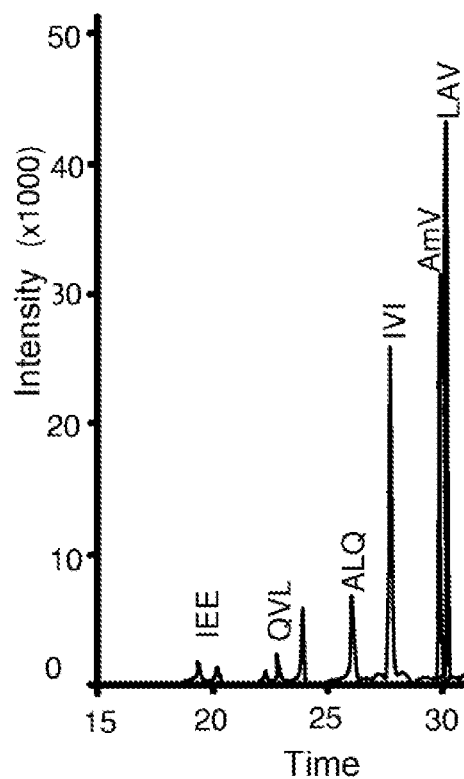
FIGS. 3A and 3B represent two chromatograms, obtained from an analysis by mass spectrometry performed on proteins obtained, respectively, from a preparation performed in part on the device of the invention and from a preparation performed manually and conventionally.
Figure 3B:
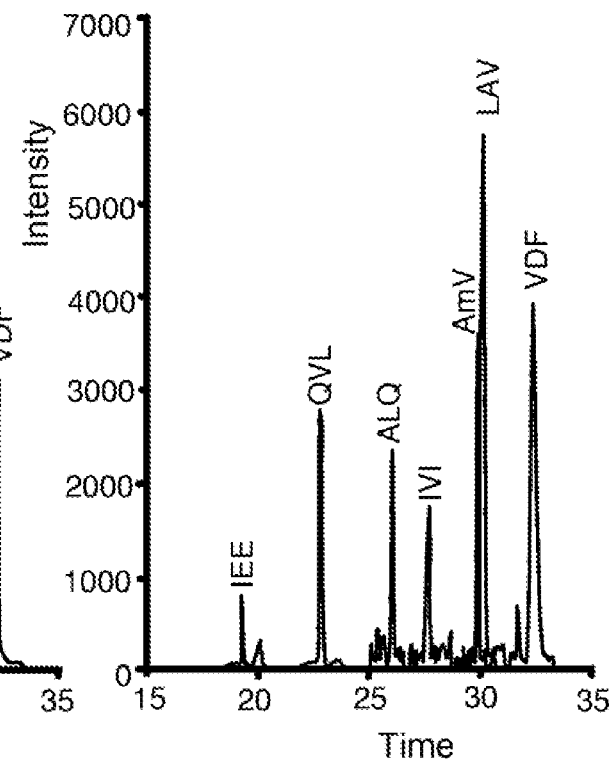

The principle of the invention which consists in employing the same card for performing all the steps for preparing the blood sample has many advantages and makes it possible to obtain particularly convincing results. It has been found, in point of fact, that the eluted and analyzable amount of the various peptides derived from the digestion of the target proteins of interest is much larger when the preparation was performed automatically on a single device in accordance with the invention rather than after various steps manually performed successively. FIGS. 3A and 3B give an appreciation of the quality of the results obtained. The intensity of the chromatography peaks is much higher for the peptides analyzed after stabilization on the device of the invention (FIG. 3A) than for peptides analyzed after a standard manual preparation (FIG. 3B).

The invention claimed is:

1. A device for preparing a blood sample, comprising:
   a microfluidic card which includes, in order from a first end of the microfluidic card to a second end of the microfluidic card along a direction of flow of the blood sample:
   an injection channel via which the blood sample may be injected;
   a first chamber in fluid communication with the injection channel, the first chamber configured to perform a separation and/or extraction of proteins to be analyzed present in the blood sample;
   a second chamber in fluid communication with the first chamber to receive a first sample comprising proteins of different species from the first chamber, the second chamber provided with at least one enzyme so as to be configured to perform a digestion of the proteins to be analyzed which are present in the first sample to obtain a second sample including digested peptides and undigested proteins; and
   a third chamber in fluid communication with the second chamber to receive the second sample including the digested peptides and the undigested proteins, the third chamber including a reverse-phase liquid chromatography column housed therein so as to be configured to perform a purification and stabilization of the digested peptides.

2. The device as claimed in claim 1, further comprising a depletion support provided in the first chamber configured to trap proteins present in the blood sample in the first chamber.

3. The device as claimed in claim 2, wherein the depletion support includes beads provided in the first chamber, the beads being grafted with one or more uptake components corresponding to the proteins to be trapped.

4. The device as claimed in claim 2, wherein the depletion support includes pillars positioned in the first chamber, the pillars being grafted with one or more uptake components corresponding to the proteins to be trapped.

5. The device as claimed in claim 2, wherein the first chamber is in a form of a coil in which surfaces of the coil form the depletion support.

6. The device as claimed in claim 1, further comprising an enrichment support present in the first chamber configured to bind and enrich the proteins to be analyzed which are present in the blood sample.

7. The device as claimed in claim 6, wherein the enrichment support includes beads present in the first chamber, the beads being grafted with one or more enrichment components corresponding to the proteins to be enriched.

8. The device as claimed in claim 6, wherein the enrichment support includes pillars positioned in the first chamber, the pillars being grafted with one or more enrichment components corresponding to the proteins to be enriched.

9. The device as claimed in claim 6, wherein the first chamber is in a form of a coil in which surfaces of the coil form the enrichment support.

10. The device as claimed in claim 1, wherein the second chamber includes a surface at least partially covered with the at least one enzyme.

11. The device as claimed in claim 1, wherein the second chamber includes an internal volume intended for storing the at least one enzyme.

12. The device as claimed in claim 1, further comprising an intermediate stabilization chamber located downstream of the first chamber and upstream of the second chamber and configured to stabilize the proteins extracted in the first chamber.

13. The device as claimed in claim 1, further comprising an initial separation chamber, located upstream of the first chamber when the first chamber is devoted to extraction of proteins.

14. The device as claimed in claim 1, further comprising separation means configured to separate plasma and blood cells present in the blood sample, arranged upstream of the first chamber.

15. The device as claimed in claim 1, further comprising plural secondary channels, each of the secondary channels being in fluid communication with one of the chambers.

16. A system for preparing a blood sample, comprising:
    a programmable robot;
    a device for preparing a blood sample as claimed in claim 1; and
    wherein the programmable robot includes a processing unit configured to run software modules to generate orders for actuators in a given sequence as a function of operation for preparing the blood sample on the device.

17. A process for preparing a blood sample, performed in the device for preparing a blood sample as defined in claim 1 and comprising:

extracting in the first chamber proteins to be analyzed which are present in the blood sample and/or separation to separate plasma from blood cells in the blood sample;

digesting in the second chamber the proteins to be analyzed which are present in a first sample comprising proteins of different species to be analyzed for obtaining a second sample including digested peptides and undigested proteins;

separating in the third chamber between the digested peptides and the undigested proteins.

18. The process as claimed in claim 17, wherein the extracting is performed by depletion of major proteins of the plasma or enrichment in the proteins to be analyzed.

19. The process as claimed in claim 17, wherein the separating is performed by liquid chromatography on a reverse-phase column.

* * * * *